United States Patent
Ball et al.

(10) Patent No.: US 10,867,705 B2
(45) Date of Patent: Dec. 15, 2020

(54) PREDICTING HEALTH OUTCOMES

(71) Applicant: ANCESTRYHEALTH.COM, LLC, Lehi, UT (US)

(72) Inventors: Catherine A. Ball, Mountain View, CA (US); Kenneth G. Chahine, Park City, UT (US); Mathew J. Barber, Chicago, IL (US); Julie M. Granka, San Francisco, CA (US)

(73) Assignee: AncestryHealth.com, LLC, Lehi, UT (US)

( * ) Notice: Subject to any disclaimer, the term of this patent is extended or adjusted under 35 U.S.C. 154(b) by 537 days.

(21) Appl. No.: 15/524,612

(22) PCT Filed: Nov. 6, 2015

(86) PCT No.: PCT/US2015/059618
§ 371 (c)(1),
(2) Date: May 4, 2017

(87) PCT Pub. No.: WO2016/073953
PCT Pub. Date: May 12, 2016

(65) Prior Publication Data
US 2018/0301227 A1     Oct. 18, 2018

Related U.S. Application Data

(60) Provisional application No. 62/076,308, filed on Nov. 6, 2014.

(51) Int. Cl.
*G16H 10/60*     (2018.01)
*G16H 50/30*     (2018.01)
(Continued)

(52) U.S. Cl.
CPC ............. *G16H 50/30* (2018.01); *G06Q 10/10* (2013.01); *G16B 10/00* (2019.02); *G16B 20/00* (2019.02);
(Continued)

(58) Field of Classification Search
CPC ........ G16H 50/30; G16H 10/60; G16H 50/20; G16B 20/00; G16B 30/00; G16B 50/00;
(Continued)

(56) References Cited

U.S. PATENT DOCUMENTS

| | | |
|---|---|---|
| 6,570,567 B1 | 5/2003 | Eaton |
| 6,760,731 B2 | 7/2004 | Huff |

(Continued)

FOREIGN PATENT DOCUMENTS

| | | |
|---|---|---|
| KR | 10-2000-0072527 A | 12/2000 |
| WO | WO 2001/016860 A2 | 3/2001 |

(Continued)

OTHER PUBLICATIONS

Browning, B.L. et al., "A Unified Approach to Genotype Imputation and Haplotype Phase Inference for Large Data Sets of Trios and Unrelated Individuals," The American Journal of Human Genetics, Feb. 13, 2009, pp. 210-223, vol. 84.

(Continued)

*Primary Examiner* — Maroun P Kanaan
(74) *Attorney, Agent, or Firm* — Fenwick & West LLP

(57) ABSTRACT

Described are methods for identification of likelihood of health outcomes such as the development of a medical condition using health histories from genetically related individuals. Embodiments include: receiving a first set of genetic data associated with the human subject; comparing the first set of genetic data to a plurality of sets of genetic data from a plurality of other individuals; identifying from the comparison a family network comprising individuals (Continued)

genetically related to the human subject as defined by identity by descent; receiving a set of health history data for each individual and each individual in the family network; analyzing the set of health history data to generate a health outcome score for the human subject, the health outcome score being a measure of risk for the human subject to develop a pre-defined health outcome that is associated with the health outcome score; and reporting the health outcome score.

20 Claims, 4 Drawing Sheets

(51) Int. Cl.
*G16B 10/00* (2019.01)
*G16B 20/00* (2019.01)
*G06Q 10/10* (2012.01)
*G16H 50/20* (2018.01)
*G06Q 10/08* (2012.01)

(52) U.S. Cl.
CPC ............ *G16H 10/60* (2018.01); *G16H 50/20* (2018.01); *G06Q 10/087* (2013.01)

(58) Field of Classification Search
CPC ........ G16B 25/00; G16B 30/10; G16B 30/20; G16B 40/00; G16B 50/30
See application file for complete search history.

(56) References Cited

U.S. PATENT DOCUMENTS

| | | | |
|---|---|---|---|
| 8,156,158 | B2 | 4/2012 | Rolls et al. |
| 8,224,862 | B2 | 7/2012 | Sacks |
| 8,275,635 | B2 | 9/2012 | Stivoric et al. |
| 2002/0128860 | A1 | 9/2002 | Leveque et al. |
| 2003/0233377 | A1 | 12/2003 | Kovac |
| 2004/0134440 | A1 | 7/2004 | Da et al. |
| 2005/0032066 | A1 | 2/2005 | Heng et al. |
| 2005/0074795 | A1 | 4/2005 | Hoffman et al. |
| 2006/0136143 | A1 | 6/2006 | Avinash et al. |
| 2006/0173663 | A1 | 8/2006 | Langheier et al. |
| 2007/0026603 | A1 | 2/2007 | Lee et al. |
| 2007/0027636 | A1 | 2/2007 | Rabinowitz |
| 2008/0133270 | A1 | 6/2008 | Michelson et al. |
| 2008/0228768 | A1 | 9/2008 | Kenedy et al. |
| 2009/0299767 | A1* | 12/2009 | Michon .................. G06Q 50/24 705/3 |
| 2009/0307181 | A1 | 12/2009 | Colby et al. |
| 2010/0199222 | A1 | 8/2010 | Kranik et al. |
| 2014/0329719 | A1* | 11/2014 | Sulem .................... G16B 99/00 506/16 |
| 2015/0112884 | A1* | 4/2015 | Ostrovsky .............. G16B 50/00 705/325 |
| 2016/0026755 | A1 | 1/2016 | Byrnes et al. |
| 2017/0329924 | A1* | 11/2017 | Macpherson .......... G16H 50/30 |

FOREIGN PATENT DOCUMENTS

| | | |
|---|---|---|
| WO | WO 2016/061260 A1 | 4/2016 |
| WO | WO 2016/061568 A1 | 4/2016 |

OTHER PUBLICATIONS

Browning, S.R. et al., "Identity by Descent Between Distant Relatives: Detection and Applications," Annual Reviews Genetics, 2012, pp. 617-633, vol. 46.

Gusev, A. et al., "Whole Population, Genome-wide Mapping of Hidden Relatedness," Genome Research, Feb. 2008, pp. 318-326, vol. 19, No. 2.

Howie, B.N. et al., "A Flexible and Accurate Genotype Imputation Method for the Next Generation of Genome-wide Association Studies," PLoS Genetics, Jun. 2009, 15 pages, vol. 5, Issue 6, e1000529.

Kong, A et al., "Detection of Sharing by Descent, Long-Range Phasing and Haplotype Imputation," Nature Genetics, Sep. 2008, pp. 1068-1075, vol. 40, No. 9.

Marchini, J. et al., "Genotype Imputation for Genome-Wide Association Studies," Nature Reviews Genetics, Jul. 2010, pp. 499-511, vol. 11, No. 7.

Palin, K. et al., "Identity-by-Descent-Based Phasing and Imputation in Founder Populations Using Graphical Models," Genetic Epidemiology, Dec. 2011, pp. 853-860. vol. 35, No. 8.

Setty, M.N. et al., "HLA Type Inference Via Haplotypes Identical by Descent," RECOMB 2010, LNBI 6044, B. Berger (Ed.), 2010, pp. 491-505.

Setty, M.N. et al., "HLA Type Inference Via Haplotypes Identical by Descent," Journal of Computational Biology, Mar. 2011, pp. 483-493, vol. 18, No. 3.

European Extended Search Report, European Application No. 15857150.5, dated Mar. 21, 2018, 8 pages.

Uricchio, L.H. et al., "Accurate Imputation of Rare and Common Variants in a Founder Population From a Small Number of Sequenced Individuals: Accurate Imputation of Rare and Common Variants," Genetic Epidemiology, May 2012, pp. 312-319, vol. 36, No. 4.

PCT International Search Report & Written Opinion, International Application No. PCT/US2015/059618, dated Feb. 29, 2016, 15 Pages.

Moltke, I. et al. "A method for detecting IBD regions simultaneously in multiple individuals—with applications to disease genetics," *Genome research*, 2011, vol. 21, No. 7, pp. 1168-1180.

Zimmerman, N.H. et al., "ChMP: a collaborative medical history portal," AMIA Annual Symposium Proceedings, 2008, American Medical Informatics Association, 5 pages.

* cited by examiner

PREDICTING HEALTH OUTCOMES

CROSS-REFERENCE TO RELATED APPLICATIONS

This application claims the benefit of U.S. Provisional Application No. 62/076,308, filed on Nov. 6, 2014, which is incorporated by reference herein in its entirety.

BACKGROUND

Field

This disclosure relates generally to predicting a health outcome, e.g., a likelihood of developing a disease and/or being a carrier for a genetic disease, for a human subject. The models and methods use health histories and family relationships based on genetic and genealogical information.

Description of Related Art

One of the current challenges in genomic medicine is that the amount of genomic information is growing rapidly and the ability to extract relevant and valuable medical information is increasingly complex. Some approaches to providing medical information rely on human-generated indices and curating the literature for associations between SNPs (single nucleotide polymorphisms) and risk of disease. This approach suffers problems including delivering low-quality results and lacking scalability.

SUMMARY

Disclosed herein are systems and methods for generating a health outcome score, e.g., a likelihood of developing a disease and/or being a carrier for a genetic disease, for a human subject. In some embodiments, the health outcome score is used to prescribe and/or tailor medical treatments for the human subject. In some embodiments, the medical treatments are preventive and/or individualized in nature. In some embodiments, the medical treatments include administering pharmaceutical compounds or drugs to the human subject.

In some embodiments, the methods include: receiving a first set of genetic data associated with the human subject; comparing the first set of genetic data to a plurality of sets of genetic data from a plurality of other individuals; identifying from the comparison a family network comprising individuals genetically related to the human subject as defined by identity by descent; receiving a set of health history data for each individual and each individual in the family network; analyzing the set of health history data to generate a health outcome score for the human subject, the health outcome score being a measure of risk for the human subject to develop a pre-defined health outcome that is associated with the health outcome score; and reporting the health outcome score.

In some embodiments, the method includes the step of receiving a set of health history data for each individual in the family network instead of the step of receiving a set of health history data for each individual and each individual in the family network.

Genetic data is used to identify a set of individuals genetically related to the human subject, i.e., identifies the human subject's family network. In some embodiments, genealogical information is provided by users of a genealogical research service or collected from other sources and used to create family trees for each of the users. DNA samples are also received from the users and analyzed. By comparing the results of the DNA analysis, potential genetic relationships can be identified between some users. Once these DNA-suggested relationships have been identified, common ancestors can be sought in the respective family trees of the potentially related users. Where these common ancestors exist, an inference can be drawn that the DNA-suggested relationship accurately represents a familial overlap between the individuals in question. People descended from a common ancestor are each members of a family network, though no single genealogical tree compiled by a single user may yet include all of the members of the network. In various embodiments, members of a family network not in a user's tree may be identified for the user using data. In some embodiments, family networks are generated in another manner, for example as described below.

For a family network, a set of health history data of individuals in the family network (in addition to a set of health history data for the human subject) is received. In some embodiments, health history data includes the presence or absence of a disease; the presence or absence of a disease-associated allele; the presence or absence of identity-by-descent (IBD) DNA, e.g., a haplotype, associated with a disease associated allele; and the age or age of death for each individual in the family network. The family network health history dataset is analyzed to generate a health outcome score for the human subject. The size of a family network can be, for example, greater than 100, 1000, 5000, or greater than 10,000 individuals.

The health outcome can include likelihood of carrier status for a genetic disease, e.g., cystic fibrosis, sickle cell anemia, or Tay Sachs disease. The health outcome can include, but are not limited to likelihood of development of a disease, e.g., a cancer, an allergy; Type II diabetes, and multiple sclerosis. The health outcome can include likelihood of responsiveness or sensitivity to a drug and the like. Some embodiments include other health outcome can be readily envisioned by a person known in the art.

The described embodiments use data related to the health outcome, e.g., health history data, from individuals in the family network. In some embodiments, health history data includes (but is not limited to) presence or absence of an allele, presence or absence of a DNA segment (haplotype) known or likely to include an allele, the presence or absence of a disease, or age or age of death. The health history data can also include date of birth, location of birth, gender, residence location, work location, environmental background, ethnicity, age of onset of a disease, age, height, weight, vaccination history, medical test results, diet, additional medical history, and the like. The health history data can include the degree of relationship between family network individuals and/or the human subject.

In some embodiments, genome-wide genetic data having at least 700,000 SNPs covering the 23 chromosomes is used. In some embodiments, methods use genetic data having sex chromosomal genetic data. In some embodiments, genetic data having mitochondrial genetic data is used.

In some embodiments, the methods include using genealogical information, e.g., information from family trees of the human subject and/or individuals in the family network and analyzing health history data from family tree members.

In some embodiments, the method further includes providing to the human subject a recommendation to obtain a medical test related to the health outcome.

Also included are computer implemented methods, systems, and computer program products for performing the methods described herein.

DETAILED DESCRIPTION

Figure 1:
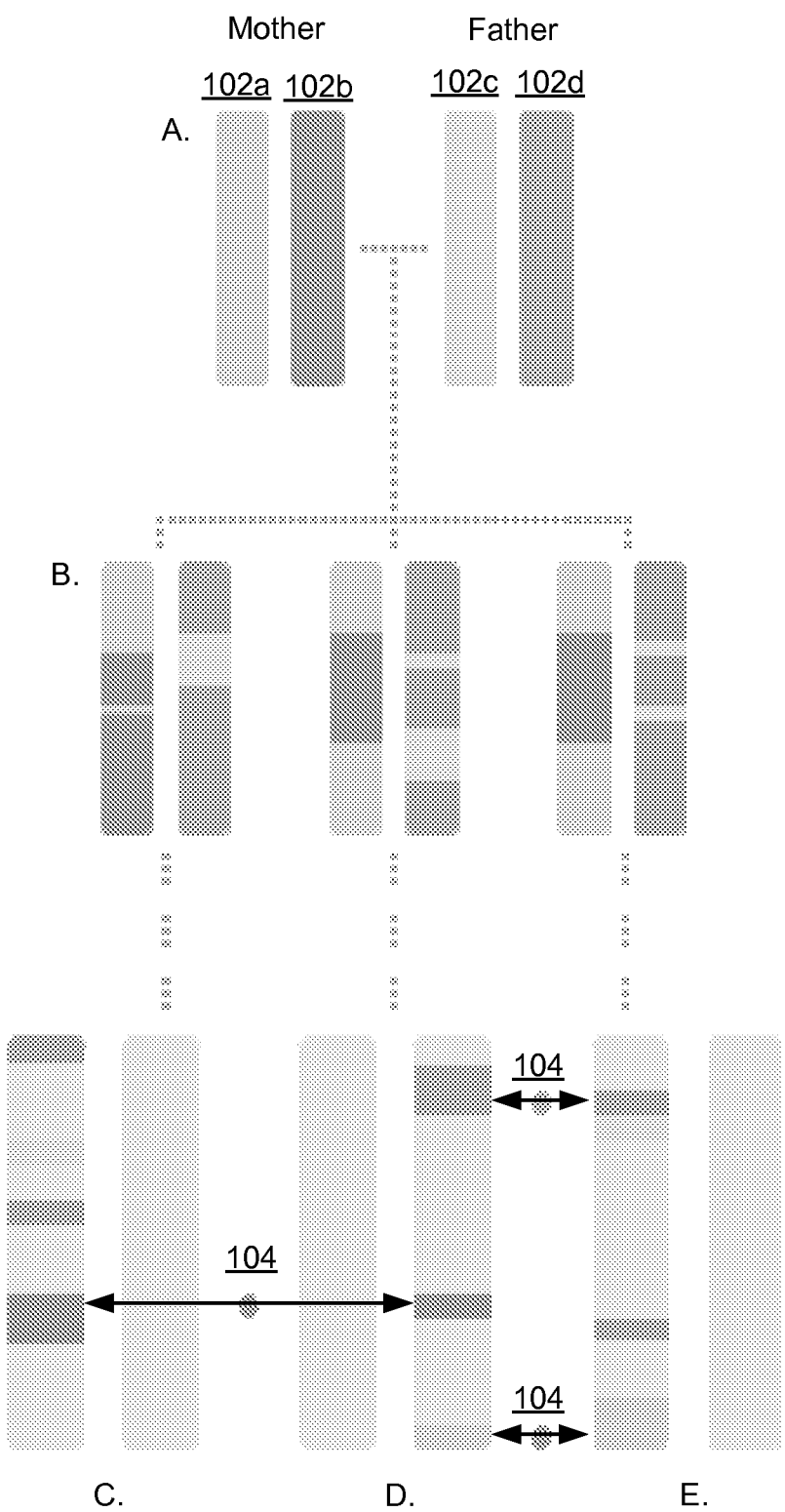
FIG. 1 is an illustration of cousin-level identical by descent (IBD) DNA, according to some embodiments

The described embodiments enable generation of a health outcome score, e.g., a likelihood of developing a disease, or being a carrier for a genetic disease, or having a particular life expectancy, for a human subject. The described embodiments use genetic data to identify a set of individuals genetically related to the human subject, i.e., identifies the human subject's family network. A family network set of data related to the health outcome is generated that includes health history data (e.g., presence or absence of a disease; presence or absence of a disease-associated allele; presence or absence of IBD DNA, e.g., a haplotype, associated with a disease associated allele; age or age of death) for each individual in the family network. In a family network the set of health history data is analyzed to generate a health outcome score for the human subject.

The methods report a health outcome score, e.g., a health hint, to a human subject that can be used for making further decisions about obtaining additional medical tests.

The methods have a greater predictive power, mitigate the risk of genotype errors, scales over time, face lower regulatory hurdles, and ultimately provide greater value to consumers compared to other genetic medical tests in the art.

Described embodiments include seeding of a database with known disease affected individuals or with carriers.

Furthermore, a million or more people in the database make the task of using IBD to infer unobserved genetic data computationally very demanding. The methods described are built to perform well with that size of database.

Genetic Data

Methods for generating a health outcome score described herein uses genetic data for identifying a family network of individuals genetically related to the human subject as described herein. In some embodiments, genetic data is also included in the health history data, e.g., in some embodiments the health history data includes sequence or other genetic information for particular alleles or haplotypes relevant to the health outcome.

The genetic data can be any type well known to one of skill in the art, including genomic DNA sequences, mRNA sequences, protein sequences and the like. For identifying a family network, genomic DNA genotyping information can be used as described in more detail below.

The genetic data can be SNP data, partial sequence data, or complete sequence data. The sequence data can be from a single locus or from multiple loci or genome-wide. The genetic data can be generated using any method well known to one of skill in the art including but not limited to chips, microarrays, genotyping arrays, or next generation sequencing technologies.

In one embodiment, the genetic data is the result of genotyping of over 700,000 SNPs across the human genome obtained using a 730K Illumina OmniExpress Chip.

Family Networks

In one embodiment, the methods include identification of a family network, e.g., a set of individuals genetically related to the human subject. The family network is identified using the genetic data. In one embodiment, the family network is identified using population-level IBD, as described herein. In one embodiment, the family network is identified using cousin-level IBD, as described herein.

In one embodiment, the GERMLINE algorithm is used to identify shared segments of genotype data due to cousin-level IBD between users. The GERMLINE algorithm is described in Gusev A, Lowe J K, Stoffel M, Daly M J, Altshuler D, Breslow J L, Friedman J M, and Pe'er I (2008) *Whole population, genomewide mapping of hidden relatedness*, Genome Res., February 19 (2): 318-26, the contents of which are incorporated by reference herein in its entirety for all purposes.

In some embodiments, the JERMLINE algorithm, an adaptation of GERMLINE; the TIMBER algorithm; and the UnderDog algorithm are used alone or in combination. In another embodiment, other methods are used for finding cousin-level IBD. One example is RefinedIBD described in Browning B L and Browning S R (2013) *Improving the Accuracy and Efficiency of Identity by Descent Detection in Population Data*, Genetics, 194: 459-471, the contents of which are incorporated by reference herein in its entirety for all purposes.

JERMLINE methods and systems are described in U.S. patent application Ser. No. 14/029,765, filed Sep. 17, 2013. TIMBER methods and systems are described in International patent application no. PCT/US2015/055579 filed on Oct. 14, 2015. UnderDog methods and systems are described in International patent application no. PCT/US2015/056164, filed on Oct. 19, 2015. The contents of these three applications are incorporated herein by reference in their entirely for all purposes.

Health Outcomes

The methods provide a likelihood of a health outcome to a human subject. The term "health outcome" includes but is not limited to likelihood of the presence or absence of a disease associated allele; likelihood of the presence or absence of an IBD DNA, e.g., a haplotype, associated with a disease associated allele; likelihood of developing a disease, and likelihood of a particular life expectancy.

In one embodiment, the methods are used to predict carrier status for a rare recessive monogenic disease where the disease-causing variant has a precisely known genomic location.

In other embodiments, the methods are used to predict carrier status of a disease causing variant where the precise genomic location (down to the base pair) is not available, e.g., the disease-causing variant is only localized to a genomic region of a given size. In these embodiments, the methods could require IBD across that entire locus.

In other embodiments, a general genomic location of the disease is not known. In this embodiment, the methods can use pairwise cousin-level IBD to discover that general genomic location. This exercise is called a "linkage analysis" when performed solely within a family, or within a set of families (Ott 1999) and "Identity-by-Descent Mapping"

for both "within population cohorts", and "within and between families" as described in, e.g., Browning and Browning 2012.

In some embodiments, the health outcome is the likelihood of the presence or absence of a disease associated allele or the likelihood of the presence or absence of IBD DNA, e.g., a haplotype, associated with a disease associated allele. The health outcome can include likelihood of carrier status for a genetic disease, e.g., cystic fibrosis, sickle cell anemia, and Tay Sachs disease.

Health outcomes can include likelihood of carrying a recessive or dominant gene for a disease. In some embodiments, the disease is monogenic; in other embodiments, the disease is caused by more than one variant or more than one gene.

In some embodiments, the methods identify carriers or a disease causing allele. In other embodiments, the methods also identify affected individuals.

In other embodiments, the health outcome can include likelihood of development of a disease. Examples include but are not limited to a cancer, an allergy; Type II diabetes, and multiple sclerosis. In some embodiments, the health outcome can include likelihood of responsiveness or sensitivity to a drug. In some embodiments, the health outcome is likelihood of a quantitative trait, e.g., high blood pressure.

Health History Data

The methods analyze health history data from family network individuals. The type of health history data will depend on the health outcome. For example, when the health outcome is the likelihood of the presence or absence of a disease associated allele, in some embodiments, the health history data will include genetic data from family network individuals. When the health outcome is likelihood of developing a disease, in some embodiments, the health history data will also include medical history related to the disease. When the health outcome is likelihood of life expectancy, the health history data will also include age or age of death from family network individuals.

In some embodiments, the health history data may include additional information including but not limited to date of birth, location of birth, gender, residence location, work location, environmental background, ethnicity, age of onset of a disease, medical history, age, height, weight, vaccination history, medical test results, diet, or degree of relationship between family network individuals.

Identical-by-Descent (IBD) DNA Segments

In some embodiments, the health history data is identical-by-descent DNA. For two stretches of DNA to be identical by descent (IBD) is for them to be both copied/inherited from the same stretch of DNA, present in a shared ancestor (see FIG. 1). Given that the two stretches are IBD, they are almost certainly identical by state (IBS), meaning that the sequences themselves are identical. The indirect observation of IBS via IBD can be cheaper than directly observed IBS through repeat assay of the genetic state. IBD is able to infer IBS, even when the variant(s) of interest are not known. However, the two stretches of DNA are not absolutely guaranteed to be identical by state, since any copy of a stretch of DNA can have small differences/mutations between it and the original/ancestral stretch of DNA that has been inherited. For example, every child has genetic variation (about 10 mutations) that does not exist in either parent from mutations that have occurred in the two copying/inheritance processes.

FIG. 1 provides an illustration of cousin-level IBD DNA (see below). A. shows the genomes of two parents. Each genome is represented by two blocks 102a, 102b, and 102c, 102d, respectively, indicated in Fig. through different grey-shades. B. shows the genomes of three children in the next generation. The inherited haplotypes are a "mixture" of each parents' blocks, due to the biological process called recombination. C., D., and E. show the genomes of three individual descendants many generations later. Each descendent only has small remaining fragments of the original haplotypes from the parents in A. Some of these fragments are shared between individuals C., D., and E., denoted by dots 104 and arrows connecting C. and D., and D. and E., respectively. These fragments are said to be identical by descent (IBD), as they are inherited from a common ancestor, and, barring mutation, should be identical. The grey-shading represents IBD DNA between the indicated individuals, due to inheritance of the same piece of the genome represented by the grey-shaded dot.

Genetic material is transmitted from one generation to the next by a complex process involving imperfect copying and partial inheritance. The copying phase can introduce small changes (mutations) while the inheritance process only allows for the transmission of one randomly selected copy, of the two possible, for each genomic location. Consequently at every location in the genome, one of the child's two sequences is IBD to one of the parent's two sequences. Between two siblings, any IBD they share is inherited from their parents. Between i-th order cousins the shared IBD sequences would be from the j-th great grandparents (where j is i minus 1).

On autosomal chromosomes, repeated transmission across additional generations is expected to reduce the size/length of the stretches of DNA that are IBD, and never increase it. The length of the stretches of DNA that are IBD are reduced because of homologous recombination. The more generations since a common ancestor between two people, the more opportunities that recombination has had to operate on shared stretches, which means greater reduction in the size/length of the stretches of DNA that are IBD.

IBD stretches can be classified into four classes. In some embodiments, the health history data includes IBD data from just one of these four classes. In other embodiments, the health history data includes identical-by-descent DNA from more than one of the following classes.

These classes are: 1. familial-level: stretches will be very long, around 0-4 copies/inheritances involved, 2. cousin-level: stretches of moderate length, around 4-12 copies/inheritances involved, 3. population-level: stretches of short length, around 12-500 copies/inheritances involved; 4. species-level: stretches of very short length, around 500+ copies/inheritances involved.

The transmission of a single stretch of DNA can be traced along an entire lineage of a family tree and thus the same stretch can be shared IBD with relatives all along this lineage. For a specific location in one person's genome, they will have a few familial-level IBD relatives, many cousin-level IBD relatives, and a huge number of population-level IBD relatives. The exact width of any stretch of IBD between a pair of people will vary from pair to pair, but pairs that are both from the same IBD level will roughly have the same width. An example of this in the context of cousin-level IBD is shown in FIG. 1.

Figure 2:
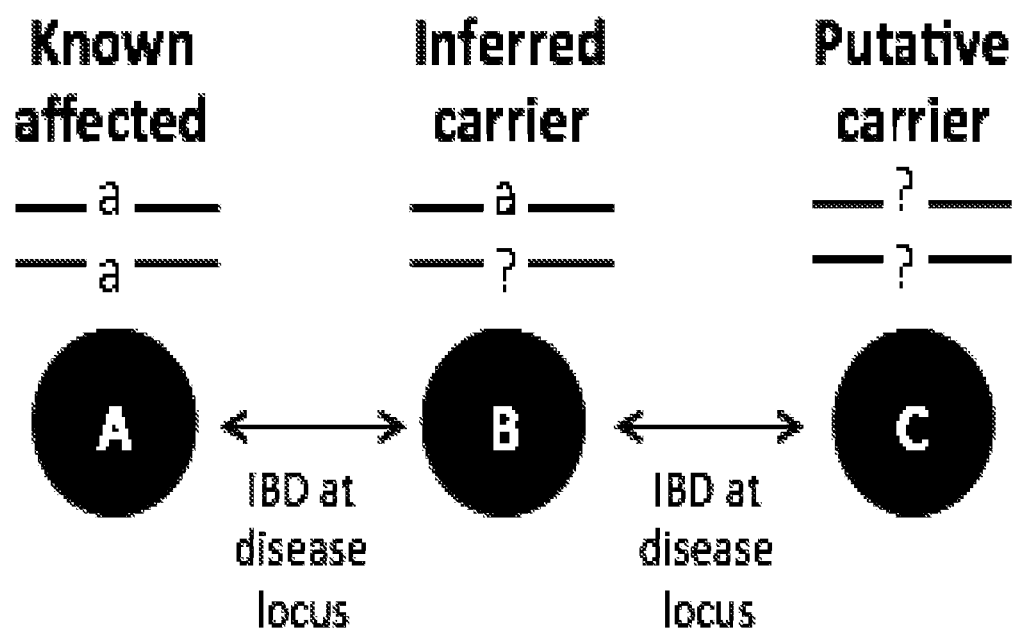
FIG. 2 is a schematic of using IBD to identify putative carriers of a disease causing allele, according to some embodiments.

An embodiment of inferences of IBS from IBD is shown in FIG. 2. In FIG. 2, an affected individual is denoted by the "A" circle. Lines above the circle indicate that the affected individual has 2 copies of the high risk, recessive genetic variant. A carrier, B, is by definition an individual with one disease-causing variant (a), and another non-disease causing variant. Carriers are identified by the methods disclosed herein by finding individuals who share DNA IBD across the disease locus with affected "A" individuals. The variant on their other genomic copy of "B" at that locus is unknown and denoted by a "?" Possible carriers C are identified by the methods disclosed herein by identifying a human subject who shares DNA IBD across the disease locus with at least one of the "B" individuals.

If a test person (C in FIG. 2) does not have observable IBD to a diseased person (A) but does have observable IBD to a known carrier, then that test person C has a 50% chance of being a carrier themselves (see FIG. 2). This is because it is easier to observe that IBD exists between two people from one point to another, but not necessarily which of the 4 possible pairs of sequences are actually IBD. In FIG. 2, for example, "C" could either share the "?" or the "a" version of the variant IBD with individual "B". However, if sequence-specific IBD could be observed, then carrier status would be inferred with certainty, leading to either a 0% or 100% evidence for person C being a carrier.

In another embodiment, in the case that a general genomic location of the disease is not known, pairwise cousin-level IBD can be used to discover that general genomic location. This exercise is called a "linkage analysis" when performed solely within a family, or within a set of families (Ott 1999) and "Identity-by-Descent Mapping" for both "within population cohorts," and "within and between families." Similar approaches are described, for example, in Browning and Browning 2012.

Health Outcome Score

The health history data is analyzed to generate a health outcome score, which in some embodiments is a likelihood that the human subject is a carrier of a genetic disease.

Using IBD to Generate a Health Outcome

In some embodiments, IBD information is used to make a disease risk prediction. In one embodiment, pairwise cousin-level IBD is used to provide general disease information/prediction in a computationally feasible manner. Cousin-level IBD is pairwise, by definition, and is more recent and wider than population-level IBD (should it exist). Although cousin-level IBD is far less frequent than population-level IBD, it is likely to be observed among a large cohort of people.

In one embodiment of the methods, presence or absence of cousin-level IBD at a specified genomic location can be used to generate the health outcome. This is because given IBD across a genomic region, IBS can also be inferred to exist across that genomic region. If that particular genomic location is known to be related to the health outcome, the inferred genomic state across that locus can be used to impute genomic variants of interest. This IBD DNA can itself be considered a health outcome or a piece of information necessary for generating the health outcome.

In one embodiment, the methods of using cousin-level IBD can be used to infer carrier status (i.e. health outcome) for a given individual. If a test person B shares a stretch of DNA IBD at the known recessive disease locus with a diseased person A, then person B can be inferred to be a carrier of high risk disease variation (see FIG. 2). Since B shares DNA IBD across the disease locus with A, even if the disease locus is not genotyped (assayed), it can be inferred to be the same (identical by state) in both A and B. Thus to infer carrier status one only needs to see that a person shares cousin-level IBD with at least one diseased person. In some embodiments, the status of IBD is observed with high accuracy resulting in an increased efficiency and accuracy of the disclosed methods. In some embodiments, the IBD in these methods is cousin-level IBD.

In another embodiment of the methods, there is an extension that is also shown in FIG. 2. The extension enhances the probability of observing a cousin-level IBD between the test person on a stretch of high-risk disease genetic variation, given that the IBD exists.

In this embodiment of the methods, if a test person (C; see FIG. 2) does not have observable IBD to a diseased person (A) but does have observable IBD to a known carrier (B) across the genomic locus of interest, then that test person C could also be inferred to be a carrier. In these methods, person C has a 50% chance of being a carrier himself (see FIG. 2). This is because it is easier to observe that IBD exists between two people from one point to another, but not necessarily, which of the 4 possible pairs of sequences are actually IBD. In FIG. 2, for example, person C could either share the "?" or the "a" version of the variant IBD with individual B. However, if sequence-specific IBD could be observed, then carrier status would be inferred with certainty, leading to either a 0% or 100% evidence for person C being a carrier. These embodiments of the methods are another application of cousin-level IBD.

In another embodiment, cousin-level IBD can be used to infer carrier or genotype status for a dominant locus, or in other embodiments, for a disease of other genetic architecture potentially spanning multiple known or unknown genomic loci. These applications can use the methods outlined above for cousin-level IBD and in the examples.

In contrast to cousin-level IBD, classically there have been two different ways in which IBD information has been used in disease risk prediction, one at the familial level and the other at the population level (see above discussion of cousin-level).

In one embodiment, familial-level IBD can also be used (albeit implicitly) when family health history is used to provide disease risk prediction. Family health history is the combination of common environmental factors shared within the family as well as common genetic factors within the family that will all be shared IBD. Familial-level IBD is also used within classical linkage analysis (Ott 1999), which is performed to localize a disease gene using within-family IBD. For most diseases, knowledge of an individual's family health history can inform an individual's risk of disease.

In one embodiment, familial level IBD can also be used to impute an individual's health outcome given health outcome variables of their family members. In a simple case, this could take the form of an inferred risk of disease given a parent's disease status.

In another embodiment of the methods for generating health outcomes, population-level IBD can enable the imputation, or inference, of the state of a particular DNA variant in a set of individuals for whom the state is unknown. Population-level IBD is being used by several known programs and algorithms (Marchini 2010). In one embodiment, the UnderDog methods are used to perform population-level IBD-based imputation to generate a health outcome. An application of UnderDog is described in the below Examples.

In this setting the key interests here are how the models can be utilized as sample sizes become large as well as the fact that the level of information about a disease variant is variable.

Population-level IBD models can be separated into two types, pairwise and non-pairwise. In one embodiment, pairwise models assess IBD between specific pairs of haplotypes, where non-pairwise models essentially use a compressed version of the pairwise data. Given the large quantity of population-level IBD, compression of the pairwise data in another embodiment, e.g., a non-pairwise model, is often a great way to improve computational speed, but at the loss of the pairwise data. A good example of a non-pairwise model is BEAGLE (Browning and Browning 2009). Two good examples of pairwise models are IMPUTE2 (Howie 2009) and SLRP (Palin 2011).

Non-pairwise algorithms can only use individuals with known state at that particular DNA variant. Such approaches enable the prediction of very specific DNA variants with high accuracy using very short, population-level tracks of IBD segments.

In one embodiment of the methods, population-level IBD inference approaches can be used to infer the genotype for a variant, or set of variants, in an individual, which can then be interpreted as a health outcome or used to further generate a health outcome.

The disadvantages of these types of population-level IBD tools are that the short stretches of DNA are only able to predict pre-specified variants. If you do not know the particular DNA variant that is to be imputed, non-pairwise population-level imputation approaches will not be useful. Moreover, if the disease is caused by a highly specific combination of variation over a longer stretch of DNA, non-pairwise population-level imputation approaches may not predict the combination with high accuracy.

Models that assess pairwise IBD up to population level are more accurate than non-pairwise models but may quickly become computationally infeasible when applied to a very large cohort. The HLA (human leukocyte antigen) region of the human genome is a great example of a region of the genome where one would prefer to impute a longer stretch of DNA (it is around three million bases long). Approaches by Kong 2008, Setty 2011 and a patent by Gilean McVean and Peter Donnelly (McVean 2008) have tackled that problem using pairwise IBD from either the population or cousin level IBD. Kong 2008 specifically use cousin-level or near cousin-level pairwise IBD to perform this task in a computationally feasible manner with a very large cohort. Palin 2011 provide a sophisticated method for the observation of cousin level or near cousin-level pairwise IBD for general imputation based on that IBD, though that algorithm does not scale for large samples.

Enrichment with Subjects with High Disease Risk (Seeding the Database)

In some embodiments, the family network set of health history data is seeded, e.g., particular individuals are added to the database to improve the methods' applicability. The general concept of seeding a database has been applied in the context of disease association studies—both case/control studies and studies that select samples given a trait value—to increase the statistical power and decrease the cost of the experiment. Such studies generally involve a comparison of "diseased" with "healthy" individuals. Within general disease assessment testing, a large number of people with disease are preferentially selected to increase statistical accuracy.

Triangulation

In some embodiments, triangulation is used to improve the use of cousin-level IBD, when that IBD is specifically used from a test person to a known carrier, when that carrier status has been inferred from a known case. Triangulation is commonly used in genetic genealogy. In triangulation, the triangle of IBD between a test person C and the persons A and B (in FIG. 2) would be assessed jointly (where persons A and B would already be known to have cousin-level IBD). Triangulation uses the fact that if person C has cousin-level IBD to a B, where that B's status has been inferred from an A, then person C must also have cousin-level IBD to that A, but it has not been observed. Triangulation would provide extra information and reduce the adverse effects of genotyping error and phasing error as well as the variable sizes of the stretches of DNA that A, B and C all share IBD, or the lack of observation of cousin-level IBD.

Triangulation can do two things at the same time. Firstly it can enhance the accuracy of the observation of cousin-level IBD between person B and person C. Secondly it can establish that the IBD is specific to the haplotype that is carrying the disease variation.

Figure 3:
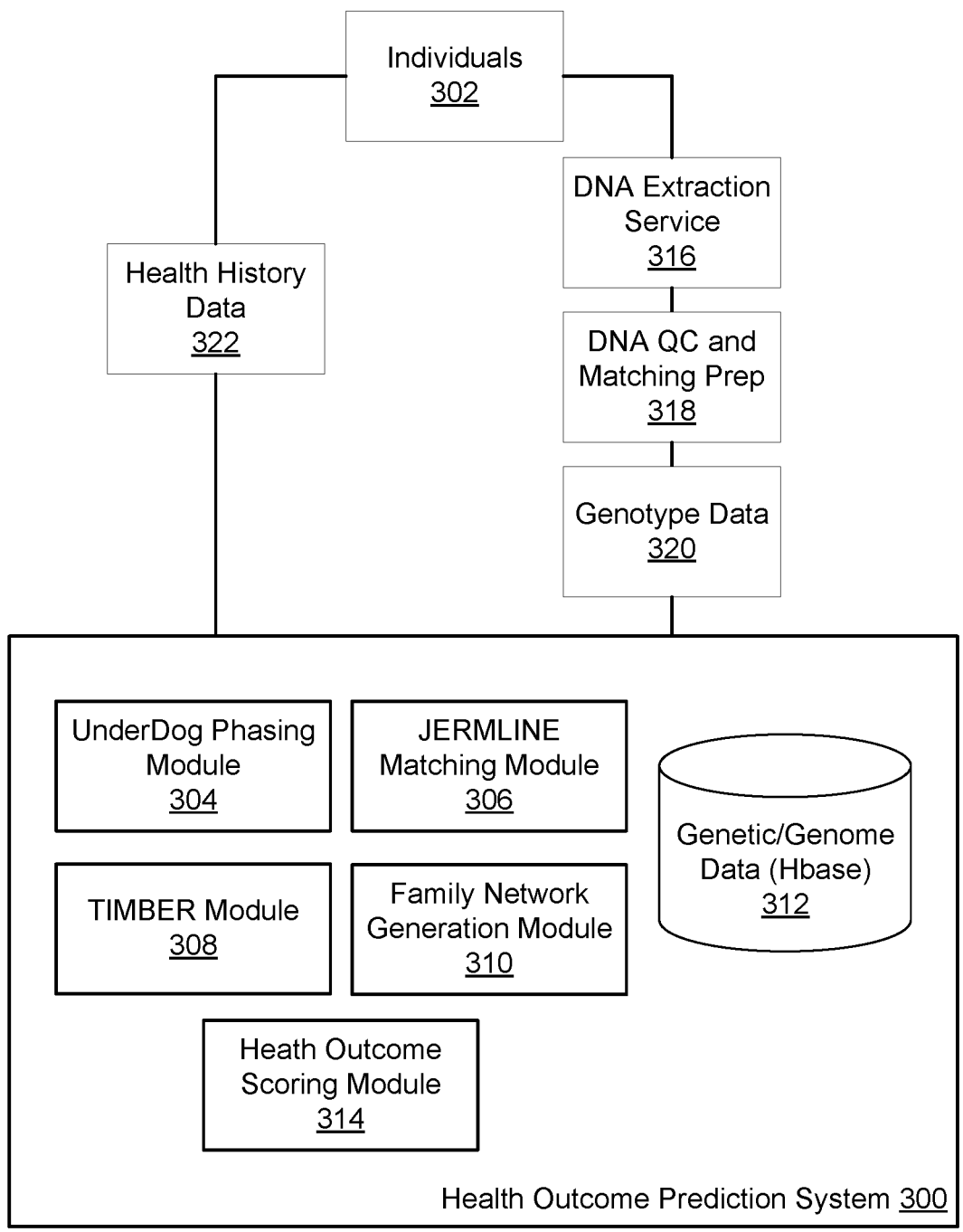
FIG. 3 illustrates a block diagram illustrating components of a system for identifying family networks and providing a health outcome score to a human subject that is part of a family network, according to some embodiments.

FIG. 3 illustrates a block diagram illustrating components of a health outcome prediction system 300 for identifying family networks and providing a health outcome score to a human subject that is part of a family network of individuals 302, according to some embodiments. The system 300 includes a UnderDog phasing module 304, a JERMLINE matching module 306, a TIMBER module 308, a family network generation module 310, a genetic/genome data (HBase) database 312, and a health outcome scoring module 314.

FIG. 3 also illustrates a DNA extraction service 316, DNA quality control (QC) matching preparation 318, and genotype data 320 that is received by the system 300. In addition, the system 300 receives the health history data 322 of the individuals 302. The database 312 can be used to store the genotype data 320 for each individual and associate the individual's corresponding health history data with the stored genotype data. In turn, the data can be accessed by each module. Each of these modules and their functions is described further herein.

For purposes of clarity within this description, we assume that system 300 is administered by or on behalf of a company providing genealogical research services to its customers, though many other use cases will be apparent from the disclosure. One example of such a company is AncestryHealth.com, LLC of Provo, Utah. Services may be provided to customers via the web, in person, by telephone, by mail, or various combinations of the above.

Figure 4:
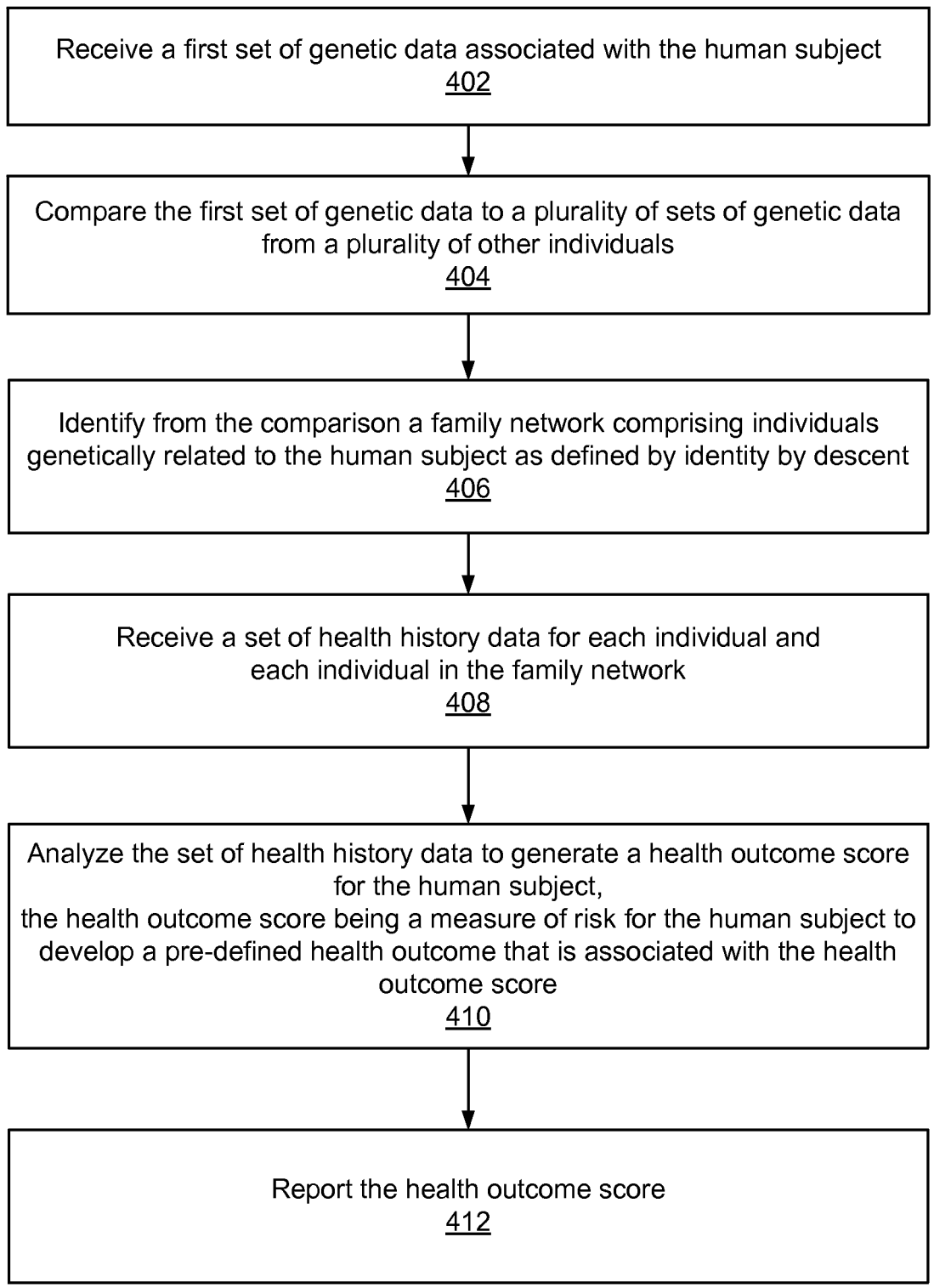
FIG. 4 illustrates a flowchart of an embodiment of the methods for providing a health outcome score to a human subject, according to some embodiments.

FIG. 4 illustrates a flowchart of an embodiment of the methods for providing a health outcome score to a human subject, according to some embodiments. In some embodiments, the methods 400 include the following steps: receiving 402 a first set of genetic data associated with the human subject; comparing 404 the first set of genetic data to a plurality of sets of genetic data from a plurality of other individuals; identifying 406 from the comparison a family network comprising individuals genetically related to the human subject as defined by identity by descent; receiving 408 a set of health history data for each individual and each individual in the family network; analyzing 410 the set of health history data to generate a health outcome score for the human subject, the health outcome score being a measure of risk for the human subject to develop a pre-defined health outcome that is associated with the health outcome score; and reporting 412 the health outcome score.

In some embodiments, the method 400 includes the step of receiving a set of health history data for each individual in the family network instead of the step of receiving 408 a set of health history data for each individual and each individual in the family network.

Alternative Embodiments

Although this description has been provided in the context of specific embodiments, those of skill in the art will appreciate that many alternative embodiments may be inferred from the teaching provided. Furthermore, within this written description, the particular naming of the components, capitalization of terms, the attributes, data structures, or any other structural or programming aspect is not mandatory or significant unless otherwise noted, and the mechanisms that implement the described invention or its features may have different names, formats, or protocols. Further, some aspects of the system may be implemented via a combination of hardware and software or entirely in hardware elements. Also, the particular division of functionality between the various system components described here is not mandatory; functions performed by a single module or system component may instead be performed by multiple components, and functions performed by multiple components may instead be performed by a single component. Likewise, the order in which method steps are performed is not mandatory unless otherwise noted or logically required.

In addition to the embodiments specifically described above, those of skill in the art will appreciate that the invention may additionally be practiced in other embodiments. Within this written description, the particular naming of the components, capitalization of terms, the attributes, data structures, or any other programming or structural aspect is not mandatory or significant unless otherwise noted, and the mechanisms that implement the described invention or its features may have different names, formats, or protocols. Further, the system may be implemented via a combination of hardware and software, as described, or entirely in hardware elements. Also, the particular division of functionality between the various system components described here is not mandatory; functions performed by a single module or system component may instead be performed by multiple components, and functions performed by multiple components may instead be performed by a single component. Likewise, the order in which method steps are performed is not mandatory unless otherwise noted or logically required. It should be noted that the process steps and instructions of the present invention could be embodied in software, firmware or hardware, and when embodied in software, could be downloaded to reside on and be operated from different platforms used by real time network operating systems.

Algorithmic descriptions and representations included in this description are understood to be implemented by computer programs. Furthermore, it has also proven convenient at times, to refer to these arrangements of operations as modules or code devices, without loss of generality.

Unless otherwise indicated, discussions utilizing terms such as "selecting" or "computing" or "determining" or the like refer to the action and processes of a computer system, or similar electronic computing device, that manipulates and transforms data represented as physical (electronic) quantities within the computer system memories or registers or other such information storage, transmission or display devices.

The present invention also relates to an apparatus for performing the operations herein. This apparatus may be specially constructed for the required purposes, or it may comprise a general-purpose computer selectively activated or reconfigured by a computer program stored in the computer. Such a computer program may be stored in a computer-readable medium, such as, but is not limited to, any type of disk including floppy disks, optical disks, DVDs, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The algorithms and displays presented are not inherently related to any particular computer or other apparatus. Various general-purpose systems may also be used with programs in accordance with the teachings above, or it may prove convenient to construct more specialized apparatus to perform the required method steps. The required structure for a variety of these systems will appear from the description above. In addition, a variety of programming languages may be used to implement the teachings above.

Finally, it should be noted that the language used in the specification has been principally selected for readability and instructional purposes, and may not have been selected to delineate or circumscribe the inventive subject matter. Accordingly, the disclosure of the present invention is intended to be illustrative, but not limiting, of the scope of the invention.

EXAMPLES

Example 1. Predicting Carrier Status for a Rare Disease and Tested Using a Test Dataset In this example, methods are described for using DNA shared identical-by-descent (IBD) to identify individuals likely to be carrying genetic variants, which are likely to cause disease, as the health outcome. First, a database of individuals is provided for whom genetic information was collected at a large number of locations across the genome (e.g. data generated using genotyping array or next-generation sequencing technologies). It is assumed that the location (on the genome) of most of the disease variants is mostly known but additional information about the disease variants is either absent in the collected data or simply unknown. Such an information level is a common outcome of many genomic analyses for disease variation.

If two people, one of whom has a disease, share genetic information identical in state (IBS) at a location known for harbouring disease variants, the other person is likely to have increased diseased risk, as the genetic variants that are IBS are much more likely to include some disease variants. Directly observing that the genetic information is identical to a diseased person can be costly and technically challenging, but identity-by-state was inferred by observing that the sequence is shared identical-by-descent (IBD) using data from a genotyping array. If the database is seeded with many individuals that are known, either by genetic or phenotypic analysis, to carry causal mutations, which allows assigning disease risk through the use of IBD state without needing to assay the sequence state for all individuals. One can identify all individuals within the database with whom these affected individuals share DNA identical by descent. In one example, the methods use individuals sharing DNA identical by descent (at the cousin-level) at causal locations to discover those that have an increased likelihood of carrying the causal mutations.

Cousin-level IBD is pairwise, by definition, and is more recent and wider than population-level IBD (should it exist). Although cousin-level IBD is far less frequent than population-level IBD, it is likely to be observed among a large cohort of people. In this example, one specifically addresses using only pairwise cousin-level IBD to provide general disease information/prediction in a computationally feasible manner.

In this example, it was assumed that the high-risk disease genetic variant cannot be observed directly by a microarray or a sequencing machine, for either cost or technical reasons. However, the high-risk disease genetic variation is known to exist within the diseased people at a specific locus (location). The question is how to extend the knowledge about the high-risk disease genetic variation from diseased individuals to identify disease-free carriers.

The key concept for inference of carrier status is that, if a test person B shares a stretch of DNA IBD at the known disease locus with a diseased person A, then person B is inferred to be a carrier of high risk disease variation (see FIG. 2). In other words, since B shares DNA IBD across the disease locus with A, even if the disease locus is not genotyped (assayed), it can be inferred to be the same (identical by state) in both A and B. Thus to infer carrier status one only need to see that a person shares cousin-level IBD with at least one diseased person. It is important that the status of IBD is observed with high accuracy for this to work well. The IBD in this example is cousin-level IBD.

FIG. 2 presents a schematic of the methods. Lines above each blue circle indicate the two variants that each individual has at the disease locus. An "a" variant is the high-risk genetic variant. A) Affected individuals are denoted by the "A" circle. These are individual whose two sequence copies are of the disease-causing type (a and a), and thus they have the disease. B) Carriers are by definition individuals who have one disease-causing variant (a), and another non-disease causing variant. Carriers are identified by finding individuals (denoted by "B") who share DNA IBD across the disease locus with affected "A" individuals. The variant on their other genomic copy at that locus is denoted by a "?," since its identity is unknown. C) Finally, the methods attempt to recover additional carriers by finding individuals (denoted by "C") who share DNA IBD across the disease locus with "B" individuals.

There is an extension to the key concept described above that is also shown in the results section below and in FIG. 2. The extension enhances the probability of observing a cousin-level IBD between the test person and a stretch of high-risk disease genetic variation, given that the IBD exists.

If a test person (C in FIG. 2) does not have observable IBD to a diseased person (A) but does have observable IBD to a known carrier, then that test person C has a 50% chance of being a carrier themselves (see FIG. 2). This is because it is easier to observe that IBD exists between two people from one point to another, but not necessarily, which of the four possible pairs of sequences are actually IBD. In FIG. 2, for example, "C" could either share the "?" or the "a" version of the variant IBD with individual "B". However, if sequence-specific IBD could be observed, then carrier status would be inferred with certainty, leading to either a 0% or 100% evidence for person C being a carrier.

While describing these methods in the context of a monogenic recessive disease, the methods are not restricted to diseases of this type. As mentioned previously, even if the exact variant causing disease is unknown, if a particular gene or larger genomic location or locations are implicated in disease, IBD across that locus still allows the methods to be applied. The methods can still be applied in the case of other disease types and for diseases caused by multiple genes. The methods can also be applied to diseases with other genetic architectures; i.e. dominant, co-dominant, etc. This particular description of the methods allows for simple simulation of method performance as described below in the Results section.

The carrier status for a rare disease was predicted via cousin-level IBD segments. A rare disease is modeled using genetic variation observed from around 330K people.

In this instance, Cystic Fibrosis was used as an example of a rare disease, with disease status being determined by the ΔF508 risk allele. Cystic Fibrosis is one of the most common rare diseases (~100 cases in 300,000 samples). Sadly, 30,000 children in the US have Cystic Fibrosis. 4.7 M people in the US carry the ΔF508 disease allele, a genomic variant that when two copies are present, an individual will have the disease (i.e., it is a recessive disease). The frequency of the ΔF508 risk allele implies 157 carriers per diseased individual.

Ethnicity is a large factor in Cystic Fibrosis (i.e., the disease is more common in Europeans). Close relatives can also be a highly informative resource for imputing medical information without any DNA information, but for Cystic Fibrosis, if one is a carrier, there is only a ~4% chance of a close relative (parent or grand-parent) having Cystic Fibrosis (assuming no in-breeding and European ancestry).

Generating Test Data

A set of 330,000 distantly related genotyped individuals in the AncestryDNA customer database was used.

Genetic data was provided. Every individual of the 330K set was genotyped on a 730K Illumina OmniExpress microarray chip, which assays the variation at 730K single nucleotide polymorphisms, or SNPs. Around 630K SNPs passed quality control and were then phased. The phase information for an individual is the knowledge of which variant is shared with the maternal genome and which variant is shared with the paternal genome. Almost all observations of genetic variation are by variant and not by contiguous chromosome, and so phase information is inferred using a statistical model.

The family network was identified. Around 390K 'LD-thinned' SNPs were used for the assessment of IBD segments between all pairs of individuals. Cousin-level IBD was observed using an AncestryDNA implementation of the GERMLINE algorithm (Gusev 2008), called JERMLINE. The output of the JERMLINE algorithm was refined using a method called TIMBER.

TIMBER was used at various thresholds to increase the confidence that the observed cousin-level IBD match is real. As the TIMBER cutoff increases, the confidence in the observation of IBD increases, but the chance of IBD being observed decreases. In this example, IBD between pairs of people that share more than 300 cM (approximately 5% of their two sets of chromosomes), were ignored so that the results were independent from any information from close relatives.

Applying the Methods to the Test Data

The health history was obtained. About 240K SNPs were not used in the assessment of pairwise IBD segments and were available as models for the ΔF508 risk allele for Cystic Fibrosis. Several SNPs in the 240K set of SNPs that were not used for IBD inference also matched the minor allele frequency of the ΔF508 risk allele: about 1 in 65 in the general US population. Those SNPs are then thinned so as to be independent of each other, i.e., the SNPs had to be around 50 cM away from each other. This left 42 SNPs that could each mimic an allele like ΔF508 risk allele on different LD and IBD backgrounds.

Using each of these 42 SNPs, disease and carrier status were assigned to each of the 330K individuals. On average, approximately 100 "cases" were observed for each variant: individuals who each have two copies of the rare "disease-causing" variant. On average, approximately 11000 "carriers" were observed: individuals who each have one copy of the rare disease-causing variant and one copy of the common disease-free variant.

The health history data was analyzed. The cousin-level IBD-based methods (see FIG. 2) were then applied to infer carriers of each of the "disease-causing" variants among the 330K individuals. It was specified that the IBD must overlap where the test ΔF508 variant is located (i.e. infer "B" individuals from "A" individuals; see FIG. 2), but this could extend to other situations involving IBD across other genomic regions. Additional carriers were also identified from IBD with newly-identified carriers (i.e. infer "C" individuals from "B" individuals; see FIG. 2).

Results

A health outcome score ("hint") was provided. The results obtained using cousin-level IBD to predict carrier status for the 42 SNPs was compared to the "known" carrier status (described above), and is shown in Table 1.

TABLE 1

Performance of cousin-level IBD methods in predicting carriers of a high-risk disease variant.

| IBD filter | Hint from "cases" | | Hint from "carriers" | |
|---|---|---|---|---|
| TIMBER cutoff | PPV | Recall | PPV | Recall |
| 5 | 99.6 | 4.6 | 18.7 | 1.9 |
| 10 | 99.6 | 1.7 | 28.6 | 0.5 |
| 25 | 99.9 | 0.1 | 47.1 | 0.01 |

The experiments were run with several different cutoffs on the same test of SNPs. Each row has the average results across all SNPs using a different TIMBER cutoff for IBD accuracy (the higher the cutoff, the higher the confidence in the observation of IBD, but lower the chance of it being observed). Any IBD segment with a TIMBER score over the TIMBER cutoff was kept. The positive predictive value (PPV) is the probability that the carrier-status hint is correct given that a carrier-status hint is provided by the methods (i.e., the proportion of hinted carriers that are actually carriers). The recall is probability that a true carrier is hinted to be a carrier (i.e., the proportion of true carriers that are hinted).

Every person who shares an IBD segment with a "case" is highly likely to be a carrier for the disease allele (see column 2 in the table 1, showing the positive predictive value, or PPV, of this inference). This accuracy does not change when changing the way IBD is used (in different rows with different TIMBER cutoffs, the PPV remains 99.6%); however, the number of people receiving a hint decreases (shown as "recall" in column 3 of table 1). A TIMBER cutoff of 5 (row 1) results in the discovery of approximately 5% of "carriers" using cousin-level IBD to the 100 or so "cases"; this is a useful but moderate number.

In contrast, the use of cousin-level IBD to identify newly inferred carriers does not fare as well (i.e., inferring "C" individuals from "B" individuals; see FIG. 2). When the TIMBER cutoff is 5 (row 2 in Table 1), only 18.7% of the hints are to true "carriers", and those hints only identify 1.9% of the all true carriers. For PPV in this step, the maximum possible value is about 50%, as IBD is presently not haplotype specific, just region specific. The PPV approaches the maximum possible value of 50% (4th row, 4th column) given a TIMBER cutoff of 25, as observed IBD at this cutoff is very likely to be real. In contrast, in other rows (with lower TIMBER cutoffs), a large proportion of the observed IBD is not actually IBD. Thus, while the first step of these methods (inferring B from A; FIG. 2) has very good performance, the second step of these methods (inferring C from B) only moderately increases recall of carriers at the cost of decreased PPV. Triangulation, as described above, can be used.

Table 1 shows results from the first step of the methods (hinting carriers from cases, i.e., inferring B individuals from A individuals (FIG. 2)). While the PPV is nearly 100%, the recall (proportion of hinted carriers) is only ~5%. This number is likely low due to the fact that on average, only 100 "cases" existed from which to then identify carriers. Based on estimates, adding 5000 "cases" to the database (potentially obtained by encouraging diseased people to join the database) would provide almost 90% of carriers with a very high quality hint—solely from having cousin-level IBD to a diseased people. This seeding (as described above) could exclude the need to assess cousin-level IBD to newly inferred carriers (i.e., to perform the step identifying "C" individuals from "B" individuals). Seeding the database with known carriers could also be used to increase recall in this second step of the methods.

Example 2: UnderDog Implements Usage of Population-Level IBD for the Imputation of the Unknown Variant Status (Both with and without Seeding)

In this example, population-level IBD was used for the imputation of the unknown variant status as the health outcome.

Methods

The methods used to impute variants that are not observed in the test individual included UnderDog. To impute is to make an educated guess about an individual's genotype at a particular position or set of positions. UnderDog uses an algorithm that is based on the algorithm described in Browning and Browning 2009, the contents of which are incorporated by reference herein in its entirety for all purposes.

The first step for UnderDog is to build a statistical model of non-pairwise population-level genetic variation from a set of individuals who are mostly distantly related to the test individual. The resultant model of genetic variation can then be used to impute variants that are not observed in the test individual (but which are observed in the set of individuals that are used to build the model). Underdog also phases genotypic information into haplotypic information (i.e., discovers the sequence of variants that were inherited as a unit from each parent).

UnderDog statistical models can be built differently depending on the end goal of the application to a test individual. When imputation is the main goal, it is best to focus on building models from a set of individuals where all variants at the genetic position (or positions) of interest have been observed. A new application of the methods that was explored is how to build models for the imputation of rare variants at a reduced cost.

Some variants can be so rare that one would not necessarily observe sufficient numbers of them even in a reasonably sized random sample of the population. To avoid observing a huge number of samples at very high cost, it was shown that accurate Underdog imputation models can be built from samples that have been selected to have a high chance of having the rare variants of interest. This is in effect enriching (or seeding) the samples that are used to build the models with information about the rare variants of interest, so that they can best impute the rare variants of interest.

Results

To demonstrate the ability of UnderDog to impute unobserved genetic variants of interest, the same testing framework as described for Example 1 was used, which uses cousin-level IBD. This example includes 42 SNPs used to impute the individuals' genotype, which were observed at a frequency of approximately 1%.

To test the methods described above, the genotypes of these 42 test SNPs from the test individuals were first masked. Masking the 42 test SNPs pretends that they were not already observed (though in actuality, for the purpose of testing, they have been observed in the test individuals). The test SNPs were not masked from the set of individuals used to build the UnderDog models (see Methods).

The genetic data observed for any individual used to build the Underdog model is a set of 630K SNPs. The genetic data observed for a test-individual is the same set of 630K SNPs, except for the 42 test SNPs.

The UnderDog models built here were based on a fixed-number of random samples of people from the population, without any seeding. The size of the set of individuals used to build the UnderDog models was varied, using the resultant models to impute the 42 test SNPs in a set of test individuals.

The results in Table 2 show results of imputation in 90K samples, some of which are carriers (i.e. have the disease variant), and others who do not. These 90K individuals were not included in the set of 220K, which is the largest number of individuals used to build the Underdog models.

TABLE 2

Performance of population-level IBD methods in predicting carriers of a high-risk disease variant (frequency ~1%).

| Number of samples used for Population-level IBD via UnderDog | Recall | PPV |
|---|---|---|
| 1K population-based samples | 89% | 91% |
| 5K population-based samples | 95% | 94% |
| 220K population-based samples | 98% | 98% |

Table 2 shows the high recall and PPV that can be achieved for predicting that a test individual carries a single copy of the rare allele. The larger the number of population-based samples that are used to build the models, the more accurate the prediction becomes. However, large numbers are not required for good prediction. The successful use of population-level IBD methods is dependent on how widespread that allele is in the population.

The imputations of variants at even lower frequency were also considered. As opposed to imputing variants at a frequency of 1%, models for the prediction of whether a test individual carries an even rarer variant were built, having a frequency of around 1 in 400. Using 5K population-based samples would only expect to observe 25 haplotypes that carry that very rare variant, rendering a population-based approach unfeasible.

Seeding for rare genetic variation will increase the chance of observing haplotypes that carry that rare variant. In this simulation a seed is a person that is known to have a rare variant and a common variant, but a seed could also easily be a diseased person for whom it is highly likely that they would carry the rare variant. In the case of seeding, UnderDog models were built both from the seeds as well as a set of randomly-selected individuals from the population who likely do not carry the rare variant or variants of interest. In the simulation, the seeds were randomly selected from the set of individuals that have both a rare variant and a common variant from the 200K individuals that were used to build the biggest UnderDog models. Table 3 shows these results, obtained from the same source data and 90K test individuals as for Table 2.

TABLE 3

Performance of population-level IBD methods in predicting carriers of a high-risk disease variant (frequency ~0.25%).

| Population-level IBD via UnderDog | Recall | PPV |
|---|---|---|
| 750 samples (250 seeds, 500 population-based) | ~99% | ~30% |
| 1500 samples (500 seeds, 1000 population-based) | ~99% | ~50% |

Table 3 shows that even with very few individuals (either 750 or 1500) carrying a very rare variant (a frequency of around 1 in 400), UnderDog can provide high recall for the carrier status for that very rare allele (i.e., nearly all individuals who are carriers are identified). Table 3 also shows that the PPV is lower for the variant with a frequency of 1 in 400, than for the variant with a frequency of 1 in 100 (i.e. of all individuals identified to be carriers, a smaller percentage of them are actually carriers).

However, PPV nearly doubles as the total number of samples used to build the UnderDog models doubles, meaning that very high PPV is attainable with a reasonable sample size. The combination of recall and PPV is undoubtedly better when seeding for a very rare variant of interest—this is because so few individuals (either 750 or 1500) are required to get relatively high recall and PPV.

These examples and applications thus demonstrate the utility of imputing genetic variants of interest using population-level IBD with UnderDog. They also demonstrate that the composition of individuals used to build the UnderDog models (i.e. seeding) can have a large impact on performance, especially for rare variants of interest.

REFERENCES

Browning B L and Browning S R (2009) *A unified approach to genotype imputation and haplotype phase inference for large data sets of trios and unrelated individuals*, Am. J. Hum. Genet., 84: 210-223.

Browning S R and Browning B L (2012) *Identity by Descent Between Distant Relatives: Detection and Applications*, Annu. Rev. Genet., 46: 617-633.

Gusev A, Lowe J K, Stoffel M, Daly M J, Altshuler D, Breslow J L, Friedman J M, and Pe'er I (2008) *Whole population, genomewide mapping of hidden relatedness*, Genome Res., February 19(2): 318-26.

Howie B N, Donnelly P, and Marchini J (2009) *A flexible and accurate genotype imputation method for the next generation of genome-wide association studies*, PLoS Genetics 5(6): e1000529.

Kong A, Masson G, Frigge M L, Gylfason A, Zusmanovich P, Thorleifsson G, Olason P I, Ingason A, Steinberg S, Rafnar T, Sulem P, Mouy M, Jonsson F, Thorsteinsdottir U, Gudbjartsson D F, Stefansson H and Stefansson K (2008) *Detection of sharing by descent, long-range phasing and haplotype imputation*, Nature Genet., September 40(9): 1068-75.

Marchini J and Howie B (2010) *Genotype imputation for genome-wide association studies*, Nature Rev. Genet., July 11(7): 499-511.

Ott J (1999) Analysis of Human Genetic Linkage, Baltimore, London: Johns Hopkins University Press 1999 (3rd edition).

Palin K, Campbell H, Wright A F, Wilson J F, and Durbin R (2011) *Identity-by-descent-based phasing and imputation in founder populations using graphical models*, Genet. Epidemiol., December 35(8): 853-60.

Setty M N, Gusev A, and Pe'er I (2011) *HLA type inference via haplotypes identical by descent*, J. Comput. Biol., March 18(3): 483-93.

The invention claimed is:

1. A method for providing a measure of risk for a human subject, the method comprising:
    receiving a first set of genetic data associated with the human subject, the genetic data generated from sequencing a biological sample of the human subject;
    comparing the first set of genetic data to a plurality of sets of genetic data from a plurality of other individuals;
    identifying a family network comprising one or more identity by descent (IBD) related individuals who are selected from the plurality of individuals, the IBD related individuals genetically related to the human subject, identifying the family network comprising:
        identifying, for a candidate individual, a plurality of IBD segments of the candidate individual that are shared with the human subject,
        determining the plurality of IBD segments that are shared between the candidate individual and the human subject cover a genetic locus that is linked to a health outcome,
        determining a total length of the plurality of IBD segments shared between the candidate individual and the human subject,
        comparing the total length of the plurality of IBD segments to a first non-zero length of shared IBD segments,
        comparing the total length of the plurality of IBD segments to a second length of shared IBD segments, the second length corresponding to a complete identity between two sets of genetic data, and
        selecting, responsive to the total length of the plurality of IBD segments that are shared between the candidate individual and the human subject falling in between the first length and the second length, the candidate individual as the one or more IBD related individuals in the family network;
    receiving health history data for at least one of the IBD related individuals in the family network;
    analyzing the health history data to generate a health outcome score for the human subject;
    predicting the measure of risk for the human subject to develop the health outcome based on the health outcome score; and
    reporting the predicted measure of risk for the human subject.

2. The method of claim 1, wherein identifying the family network comprises inferring cousin level identity by descent (IBD) among the plurality of sets of genetic data and inferring cousin level IBD between the plurality of sets of genetic data and the first set of genetic data associated with the human subject.

3. The method of claim 1, wherein analyzing the health history data to generate the health outcome score comprises identifying individuals who share an IBD segment that is associated with the health outcome.

4. The method of claim 1, wherein the health outcome is at least one of the following: likelihood of carrier status for a genetic disease, likelihood of developing a disease, or life expectancy.

5. The method of claim 1, wherein the health outcome is likelihood of carrier status for a genetic disease of at least one of the following: cystic fibrosis, sickle cell anemia, or Tay Sachs disease.

6. The method of claim 1, wherein the health outcome is likelihood of development of a disease of at least one of the following: a cancer, an allergy, Type II diabetes, or multiple sclerosis.

7. The method of claim 1, wherein the health outcome is responsiveness or sensitivity to a drug.

8. The method of claim 1, wherein the genetic data comprises at least 700,000 single nucleotide polymorphisms (SNPs) covering autosomal genetic data, and/or sex chromosomal genetic data and/or mitochondrial genetic data.

9. The method of claim 1, wherein the health history data comprises one or more of the following: presence or absence of an allele, presence or absence of a DNA segment known to include an allele, presence or absence of a disease, age or age of death.

10. The method of claim 1, wherein the health outcome comprises likelihood of carrier status for a genetic disease, and the health history data comprises presence or absence of a DNA segment known to include the allele.

11. The method of claim 1, wherein the health history data comprises one or more of the following: date of birth, location of birth, gender, residence location, work location, environmental background, ethnicity, age of onset of a disease, medical history, age, height, weight, vaccination history, medical test results, diet, or degree of relationship between family network individuals.

12. The method of claim 1, wherein the health history data includes data from members of a family tree of the human subject.

13. The method of claim 1, wherein comparing the total length of the plurality of IBD segments to the second length of shared IBD segments comprises comparing the total length of the plurality of IBD segments to a length less than or equal to the complete identity.

14. A computer implemented method for determining a measure of risk for a human subject, the method comprising:
    receiving, by a computer, a first set of genetic data associated with the human subject, the genetic data generated from sequencing a biological sample of the human subject;
    comparing, by the computer, the first set of genetic data to a plurality of sets of genetic data from a plurality of other individuals;
    identifying a family network comprising one or more identity by descent (IBD) related individuals who are selected from the plurality of individuals, the IBD related individuals genetically related to the human subject, identifying the family network comprising:
        identifying, for a candidate individual, a plurality of IBD segments of the candidate individual that are shared with the human subject,
        determining the plurality of IBD segments that are shared between the candidate individual and the human subject cover a genetic locus that is linked to a health outcome, determining a total length of the plurality of IBD segments shared between the candidate individual and the human subject, comparing the total length of the plurality of IBD segments to a first non-zero length of shared IBD segments, comparing the total length of the plurality of IBD segments to a second length of shared IBD segments, the second length corresponding to a complete identity between two sets of genetic data, and selecting, responsive to the total length of the plurality of IBD segments that are shared between the candidate individual and the human subject falling in between the first length and the second length, the candidate individual as the one or more IBD related individuals in the family network;

receiving, by the computer, health history data for at least one of the IBD related individuals in the family network;

analyzing, by the computer, the health history data to generate the health outcome score for the human subject;

predicting the measure of risk for the human subject to develop the health outcome based on the health outcome score; and outputting, by the computer, the predicted measure of risk for the human subject.

15. A system comprising:

one or more processors; and a memory configured to store computer code comprising instructions, the instructions, when executed by one or more processors, causing the one or more processors to perform steps comprising:

receiving a first set of genetic data associated with the human subject, the genetic data generated from sequencing a biological sample of the human subject;

comparing the first set of genetic data to a plurality of sets of genetic data from a plurality of other individuals;

identifying a family network comprising one or more identity by descent (IBD) related individuals who are selected from the plurality of individuals, the IBD related individuals genetically related to the human subject, identifying the family network comprising:

identifying, for a candidate individual, a plurality of IBD segments of the candidate individual that are shared with the human subject, determining the plurality of IBD segments that are shared between the candidate individual and the human subject cover a genetic locus that is linked to a health outcome, determining a total length of the plurality of IBD segments shared between the candidate individual and the human subject, comparing the total length of the plurality of IBD segments to a first non-zero length of shared IBD segments, comparing the total length of the plurality of IBD segments to a second length of shared IBD segments, the second length corresponding to a complete identity between two sets of genetic data, and selecting, responsive to the total length of the plurality of IBD segments that are shared between the candidate individual and the human subject falling in between the first length and the second length, the candidate individual as the one or more IBD related individuals in the family network;

receiving health history data for at least one of the IBD related individuals in the family network;

analyzing the health history data to generate a health outcome score for the human subject;

predicting the measure of risk for the human subject to develop the health outcome based on the health outcome score; and outputting the predicted measure of risk for the human subject.

16. The system of claim 15, wherein comparing the total length of the plurality of IBD segments to the second length of shared IBD segments comprises comparing the total length of the plurality of IBD segments to a length less than or equal to the complete identity.

17. The system of claim 15, wherein analyzing the health history data to generate the health outcome score comprises identifying individuals who share an IBD segment that is associated with the health outcome.

18. The system of claim 15, wherein the health outcome is at least one of the following: likelihood of carrier status for a genetic disease, likelihood of developing a disease, or life expectancy.

19. The system of claim 15, wherein the health outcome comprises likelihood of carrier status for a genetic disease, and the health history data comprises presence or absence of a DNA segment known to include the allele.

20. The system of claim 15, wherein the health history data comprises one or more of the following: date of birth, location of birth, gender, residence location, work location, environmental background, ethnicity, age of onset of a disease, medical history, age, height, weight, vaccination history, medical test results, diet, or degree of relationship between family network individuals.

* * * * *